United States Patent
Uhrenius et al.

(10) Patent No.: US 6,501,989 B1
(45) Date of Patent: Dec. 31, 2002

(54) HEART STIMULATOR HAVING AN EVOKED RESPONSE DETECTOR

(75) Inventors: Åsa Uhrenius, Stockholm (SE); Berit Larsson, Danderyd (SE); Peter Andersson, Stockholm (SE); Göran Budgifvars, Spånga (SE); Feresteh Shojael, Solna (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/719,722
(22) PCT Filed: Jun. 9, 1999
(86) PCT No.: PCT/SE99/01017
§ 371 (c)(1), (2), (4) Date: Mar. 21, 2001
(87) PCT Pub. No.: WO99/65568
PCT Pub. Date: Dec. 23, 1999

(30) Foreign Application Priority Data

Jun. 16, 1998 (SE) .................................. 9802151

(51) Int. Cl.[7] .............................................. A61N 1/362
(52) U.S. Cl. ........................................................ 607/28
(58) Field of Search ..................................... 607/27, 28

(56) References Cited

U.S. PATENT DOCUMENTS

| 5,391,192 A | 2/1995 | Lu et al. ................. 607/28 |
| 5,417,718 A | 5/1995 | Kleks et al. ................. 607/28 |
| 5,431,693 A | 7/1995 | Schroeppel ................. 607/28 |
| 5,458,623 A | 10/1995 | Lu et al. ................. 607/28 |
| 5,697,957 A | 12/1997 | Noren et al. ................. 607/28 |
| 5,741,312 A | 4/1998 | Vonk et al. ................. 607/28 |
| 5,846,264 A | * 12/1998 | Andersson et al. ........... 607/28 |
| 5,855,594 A | * 1/1999 | Olive et al. ................. 607/28 |

FOREIGN PATENT DOCUMENTS

EP 0 906 768 7/1999 ............ A61N/1/37

OTHER PUBLICATIONS

"Comparison of Unipolar and Bipolar ventricular Paced Evoked Responses," Baig et al., Br. Heart J., vol. 68 (1992), pp. 398–402.

* cited by examiner

Primary Examiner—Carl Layno
(74) Attorney, Agent, or Firm—Schiff Hardin & Waite

(57) ABSTRACT

A heart stimulator has an evoked response detector which determines evoked response in the presence of polarization. To determine the magnitude of the polarization for different stimulation amplitudes, the electrode signals picked up by a lead after the delivery of a stimulation pulse having a selected amplitude are measured. A polarization signal is obtained from the picked up signals, and this polarization signal, with modification, is subtracted from signals picked up following subsequently emitted stimulation pulses. Dependent on the subtraction result, a determination is made as to whether an evoked response has occurred.

20 Claims, 2 Drawing Sheets

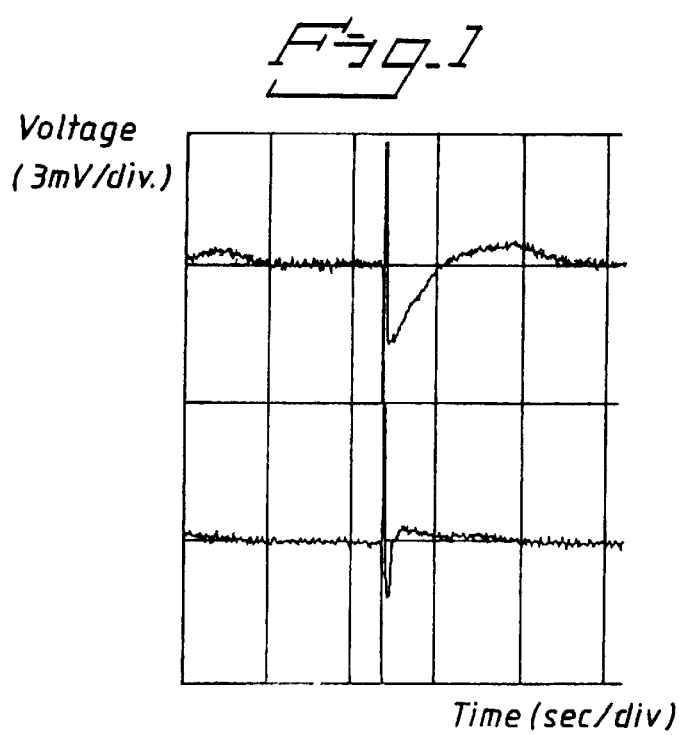
Fig. 1
Voltage (3mV/div.)
Time (sec/div)
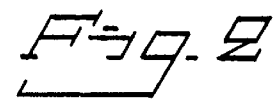
Fig. 2
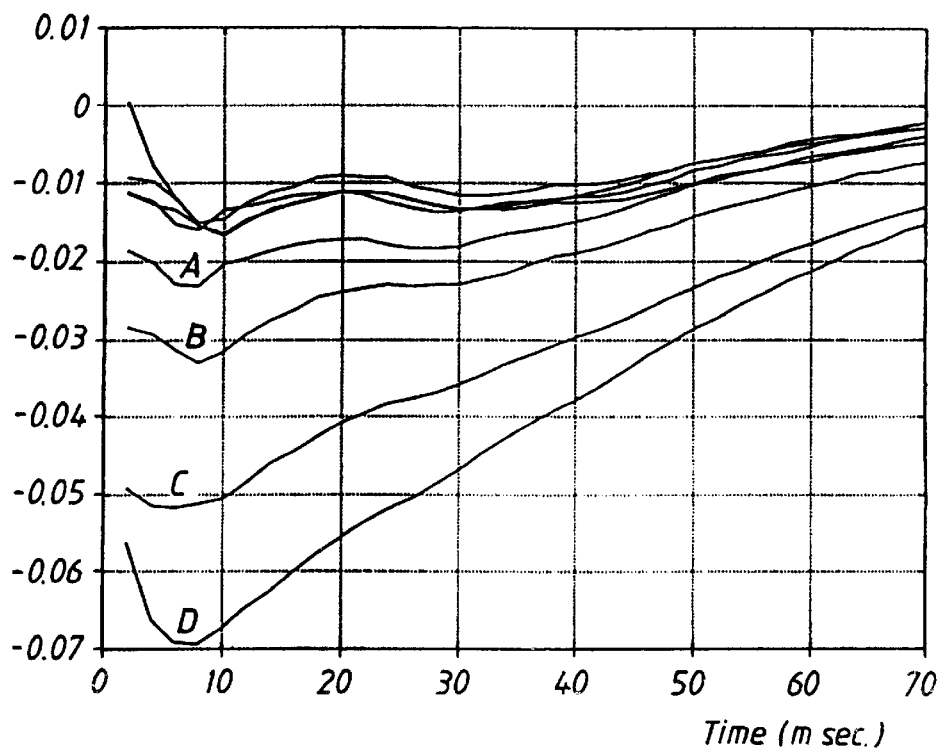

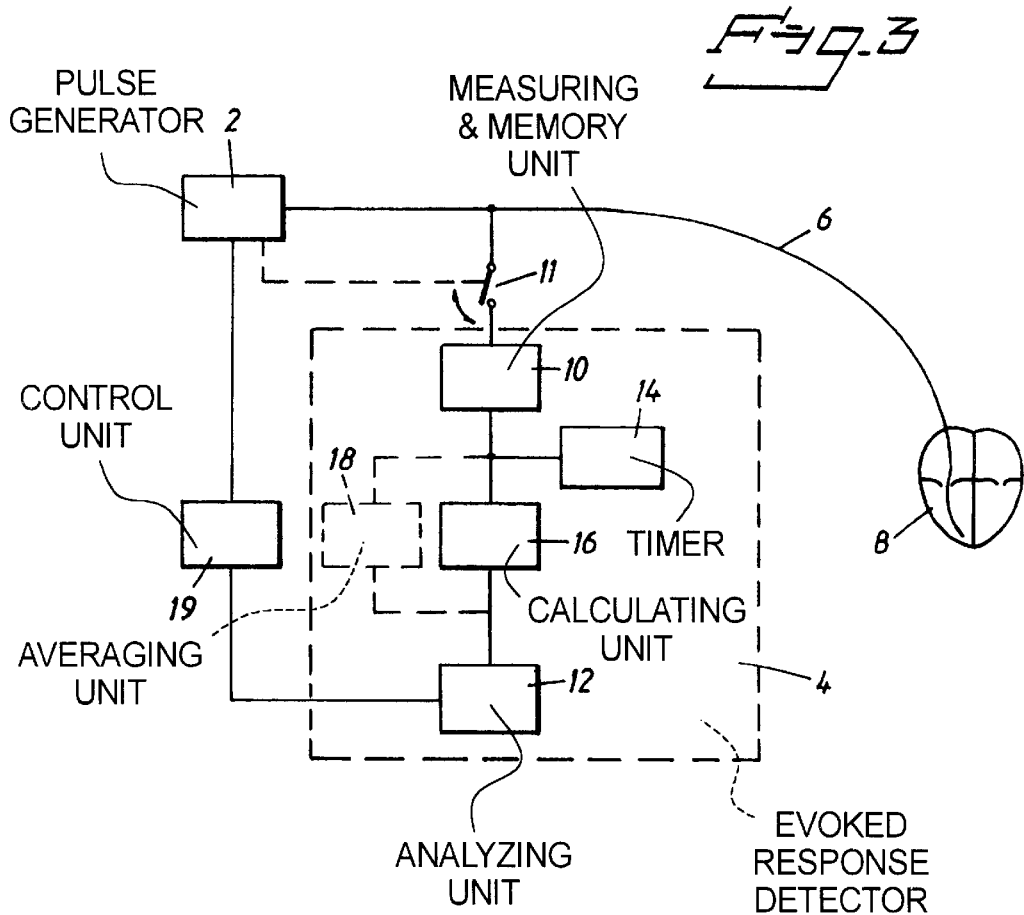
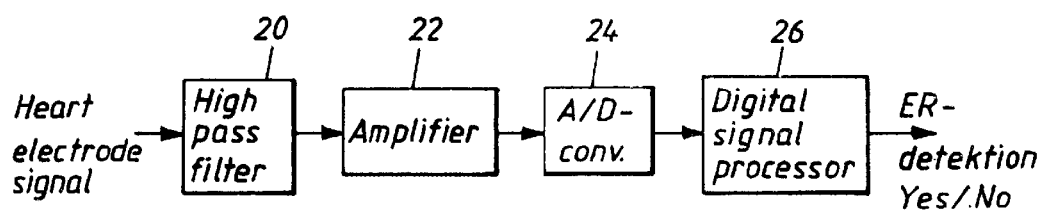

HEART STIMULATOR HAVING AN EVOKED RESPONSE DETECTOR

BACKGROUND OF THE INVENTION

1. Field of the Invention

The present invention relates to an evoked response detector for a heart stimulator for determining evoked response in the presence of polarization, the heart stimulator having a pulse generator and a control unit for controlling the pulse generator to produce stimulation pulses of varying amplitudes, and a lead being intended to be introduced into the heart of a patient and connected to the pulse generator for delivering stimulation pulses to the heart, and wherein the evoked response detector has a measuring and memory unit for measuring and storing the electrode signal picked up by the lead in response to delivered stimulation pulses.

2. Description of the Prior Art

To reduce the energy consumption of heart stimulators an automatic threshold search function, a so called AUTOCAPTURE™ function, is provided to maintain the energy of the stimulation pulses at a level just above that which is needed to effectuate capture, cf. e.g. U.S. Pat. No. 5,458,623. A reliable detection of the evoked response, which then is necessary, is, however, not a simple matter, especially when it is desired to sense the evoked response with the same electrode as the one delivering the stimulation pulse. This is because of the fact that the evoked response potential is small in amplitude compared to the residual polarization charge. The residual charge decays exponentially but tends to dominate the evoked potential for several hundreds of milliseconds after the stimulation. If the polarization is too high, it could be wrongly interpreted by the evoked response detector as a capture, i.e. contraction of the heart. The AUTOCAPTURE™ algorithm could then by mistake adjust the output amplitude of the stimulation pulse to a value below the actual capture level, which will result in no capture. If the used pacing lead has significant polarization this could consequently disturb the AUTOCAPTURE™ function and result in loss of capture.

Several attempts have been made to solve the lead polarization problems in connection with evoked response detection. One way of reducing these problems is to use special low polarizing leads.

Another method is described in U.S. Pat. No. 5,417,718, which discloses a system for maintaining capture wherein electrical post-stimulus signal of the heart, following delivery of a stimulation pulse, is compared to a polarization template, determined during a capture verification test. A prescribed difference between the polarization template and the post-stimulus signal indicates capture. Otherwise loss of capture is presumed and the stimulation energy is increased a predetermined amount to obtain capture.

In U.S. Pat. No. 5,697,957 a method and an apparatus are described for extracting an evoked response component from a sensed cardiac signal by suppressing electrode polarization components. An autocorrelation function is then calculated according to an autocorrelation algorithm and applied to the sensed cardiac signal. The autocorrelated signal thus obtained and the sensed cardiac signal are normalized and the difference between these two normalized signals is formed to thereby extract the evoked response component if it is present.

In U.S. Pat. No. 5,741,312 a method and an apparatus are described to determine stimulating threshold through delivery pulse pairs consisting of a first lower amplitude search pulse with variable amplitude and a second regular pacing pulse within 50–100 ms. Threshold search is executed by incrementing the amplitude of the search pulse until an evoked response is detected. Alternatively the period from regular pacing pulse to the T-wave is measured and capture on the search pulse is determined as a sudden shortening of this interval. U.S. Pat. No. 5,741,312 further discusses methods to minimize polarization by optimizing pulse parameters of a two- or triphasic pacing pulse. The system disclosed in U.S. Pat. No. 5,741,312 however, makes no attempt to determine the polarization free evoked response signal by subtracting polarization determined by the actual stimulation amplitude from the signal picked up by the electrode in response to a stimulation pulse.

There is mostly at least one significant slope in the bipolar measured IEGM signal, which makes it possible to discriminate the evoked response signal from slowly varying signals such as polarization signals. Thus in U.S. Pat. No. 5,431,693 a method of verifying capture of the heart by a cardiac pacemaker is described. Observing that the non-capture potential is exponential in form and the evoked capture potential, while generally exponential in form, has one or more small-amplitude perturbations superimposed on the exponential wave form, these perturbations are enhanced for ease of detection by processing the wave form signal by differentiation to form the second derivative of the evoked response signal for analysis for the evoked response detection.

Unipolar detection of evoked response signals is however not possible by this technique. Abrupt slope changes or superimposed small-amplitude perturbations are leveled out if the measurements are made over the longer distance from the electrode to the stimulator casing.

The unipolar sensed evoked response signal thus differs from the bipolar sensed evoked response signal both in duration and amplitude, see Baig et al, "Comparison of Unipolar and Bipolar Ventricular Based Evoked Responses", Br Heart J. 1992, 68: 398–402. The duration of the evoked QRS complex is a measure of total ventricular bipolarization time in the area of the heart subtended by a sensing bipole, and it depends on the extension of the bipole. This means that the unipolar evoked response signal measured between the electrode tip and the casing of the heart stimulator has a longer duration than the bipolar evoked response measured between tip and ring electrodes. This is illustrated in FIG. 1 herein in which the upper curve shows an unfiltered cardiac signal measured by a unipolar lead and the lower curve the cardiac signal sensed by a bipolar electrode. Known; evoked response detectors, the function of which is based on the detection of a slope of the evoked response signal, typically in a detection window of 15–60 msesc after the stimulation pulse, are therefore not suited for detection of evoked response by unipolar electrodes.

It has now appeared that the evoked response signal amplitude is, fairly constant, independent of the stimulation pulse amplitude, i.e. the evoked response signal amplitude does not vary with the amplitude of the stimulation pulse (provided that the stimulation amplitude is above the capture threshold). Further, it has been found that the electrode polarization is approximately linearly dependent on the stimulation pulse amplitude for a constant pulse duration, as disclosed in European Application 0906768.

SUMMARY OF THE INVENTION

An object purpose of the present invention is to provide a heart stimulator having an evoked response detector detector for determining evoked response based on the above circumstances which does not depend on any slope measurements of the sensed signal, which can be used with both low polarizing and high polarizing unipolar sensing electrode leads.

The above object is achieved in accordance with the principles of the present invention in a heart stimulator having a pulse generator which emits stimulation pulses and a lead connected to the pulse generator adapted for introduction into the heart of a patient for delivering the stimulation pulses to the heart, a control unit for varying the respective amplitudes of the stimulation pulses, and an evoked response detector for determining evoked response in the presence of polarization, the evoked response detector including a measuring and storage unit for measuring the electrode signal picked up by the lead in response to respective stimulation pulses and for storing the measurement. For determining the magnitude of the polarization for different stimulation amplitudes, in a first embodiment the control unit controls the pulse generator to emit stimulation pulses including a high amplitude stimulation pulse preceding a low amplitude stimulation pulse, the low amplitude stimulation pulse having an amplitude equal to a known stimulation threshold voltage plus a predetermined voltage step, and the high amplitude stimulation pulse having an amplitude above the amplitude of the low amplitude stimulation pulse. The measurement and memory unit measures and stores respective signals picked up by the electrode lead immediately after the high amplitude stimulation pulse and the low amplitude stimulation pulse, as well as respectively signals picked up by the electrode lead immediately following subsequent stimulation pulses which are emitted after the low amplitude stimulation pulse. A calculating unit in the evoked response detector determines a first difference between the respective signals picked up by the electrode lead immediately after the high amplitude stimulation pulse and the low amplitude stimulation pulse, and also calculates a second difference between the amplitude of the high amplitude stimulation pulse and the amplitude of the low amplitude stimulation pulse, and the calculating unit forms a quotient of the first difference and the second difference. An analyzing unit in the evoked response detector determines whether an evoked response has occurred to respective ones of the subsequent stimulation pulses by, for each subsequent stimulation pulse, determining a polarization signal by multiplying the amplitude of the subsequent stimulation pulse by the aforementioned quotient, and subtracting the polarization signal from the signal picked up by the electrode lead immediately following the subsequent stimulation pulse.

In a second embodiment, the control unit controls the pulse generator to emit a high amplitude stimulation pulse preceding a succession of lower amplitude stimulation pulses. The lower amplitude stimulation pulses have respective amplitudes which are successively lowered from the amplitude of the high amplitude stimulation pulse by a predetermined voltage step, so that the respective lower amplitude stimulation pulses have amplitudes equal to a known stimulation threshold voltage plus one or more of the voltage steps. The measuring and memory unit measures and stores respective signals picked up the electrode lead immediately after the high amplitude stimulation pulse and each of the lower amplitude stimulation pulses. The calculating unit, for each of the lower amplitude stimulation pulses, determines a difference between the signal picked up by the electrode lead after the high amplitude stimulation pulse and the signal picked up by the electrode lead and a respective lower amplitude stimulation pulse, and divides this difference by the number of voltage steps which were used to produce the lower amplitude stimulation pulse which was used to form the aforementioned difference. This result is stored as a magnitude of polarization per voltage step. The analyzing unit determines whether an evoked response has occurred to subsequent stimulation pulses, emitted after a last of the lower amplitude stimulation pulses, by determining a polarization signal by forming a quotient between the amplitude of the subsequent stimulation pulse and the voltage step, and multiplying this quotient by the polarization pervoltage step, and subtracting the polarization signal from the signal picked up by the electrode lead immediately following the subsequent stimulation pulse.

In a third embodiment, the control unit operates the pulse generator to deliver a stimulation pulse having an amplitude below the stimulation threshold value, and a calculating unit calculates the quantity $Pol_{step}=U_{measlow}/m$, wherein $U_{measlow}$ is the measured electrode signal obtained from the stimulation pulse having an amplitude below the threshold value, and m is the quotient of the low stimulation amplitude and the employed voltage step. The evoked response detector also includes an analyzing unit which determines evoked response signals by subtracting, from subsequently picked up electrode signals, a polarization signal having a magnitude equal to the quotient between the actual stimulation amplitude and the voltage step, multiplied by the stored polarization per voltage step $Pol_{step}$.

Thus in the detector according to the invention the polarization arising after a stimulation pulse which is a problem for safe detection of evoked response, is reduced to such an extent that also unipolar detection can be performed reliably. This is an important advantage since unipolar leads are less complicated to manufacture and have longer working life than bipolar electrodes. The detector according to the invention also makes it possible to determine in a reliable way when the AUTOCAPTURE™ function of a heart stimulator can be activated. Thus the use of such heart stimulators can be extended also to patients having unipolar leads. Another advantage of the detector according to the invention is that no extra stimulation pulses, resulting in extra current draining, are needed as in previously known techniques for measuring the polarization.

In an embodiment of the detector according to the invention the pulse generator is controlled to deliver at least one high amplitude stimulation pulse and one low amplitude stimulation pulse a number of times, and the measuring and memory unit measures the corresponding electrode signals picked up by the lead after each stimulation pulse for calculating the aforementioned quotient a corresponding number of times. The therefor; calculating unit forms an average quotient value of the number of quotients to be used for subsequent determination of the evoked response. The pulse generator can also be controlled to deliver a number of series of stimulation pulses, each series starting with a high stimulation amplitude pulse and ending with a low stimulation amplitude pulse, and the calculating unit determines the magnitude of the polarization per voltage step $Pol_{step}$ from electrode signals picked up from each series of pulses and forms an average value of the obtained number of polarization per voltage step $Pol_{step}$, this average value being stored for use as the stored polarization per voltage step $Pol_{step}$ for subsequent determination of the evoked response signal. For determining the evoked response signal the measuring and memory unit can further be adapted to sample the electrode signal picked up by the lead with a predetermined sampling frequency during a predetermined time interval after the delivery of a stimulation pulse for calculating a mean value of these sampled values. By these determinations of mean or average values small variations and interferences in the measured evoked response and polarization signals are suppressed.

In a further embodiment of the invention, a measuring and memory unit measures the electrode signal picked up by the lead before the delivery of a stimulation pulse to determine a DC level to be subtracted from the electrode signal picked up after the delivery of a stimulation pulse. The measuring and memory unit means can be adapted to measure the electrode signals picked up by the lead before the delivery of each stimulation pulse of the high amplitude and the low amplitude respectively and the calculation unit can be arranged to determine the average value of these measured signals prior to the stimulation pulse as the DC level to be subtracted from measurement signals picked up after the delivery of stimulation pulses. By subtracting the DC level from the measured electrode signal in this way the real magnitude of this signal is obtained.

In a further embodiment, a comparison unit compares the determined evoked response signal with a predetermined limit to determine whether capture is present or not. The pulse generator can be controlled to deliver a plurality of stimulation pulses of high stimulation amplitude and a plurality of low amplitude stimulation pulses and the calculating unit forms an average value of the plurality of evoked response signals resulting from the stimulation pulses of high amplitude and an average value of the plurality of evoked response signals resulting from the low amplitude stimulation pulses, said average values being supplied to the comparison unit for comparison with the predetermined limit value. In this way it is possible to determine not only whether capture is present or not, but also if the AUTOCAPTURE™ function of the heart stimulator can be activated or not.

DESCRIPTION OF THE DRAWINGS

FIG. 1 shows the unfiltered electrode signal picked up by a unipolar lead, as well as the unfiltered electrode signal picked up by a bipolar lead.

FIG. 2 shows the measured electrode signal for four different stimulation pulse amplitudes and the evoked response signals with the polarization signals subtracted therefrom, in accordance with the invention.

FIG. 3 is a block diagram of a heart stimulator having an evoked response detector operating in accordance with the principles of the present invention.

FIG. 4 is a block diagram of a further embodiment of an evoked response detector according to the invention.

DESCRIPTION OF THE PREFERRED EMBODIMENTS

The polarization of a pacemaker electrode can be described as $$Pol = \frac{U_{stim}}{\alpha} * f(dur, RC_{output})$$

where Pol designates the polarization signal, $U_{stim}$ the pacemaker stimulation pulse amplitude, $\alpha$ is a constant, dur designates the duration of the stimulation pulse and $RC_{output}$ is the time constant of the pacemaker output lead system, see Konrad Mund, "Analysis of the polarization and the sensing behavior of electrodes for cardiac pacemakers", Pacemaker leads, Elsevier Science Publishers BV, 1991.

Thus, according to the equation above the polarization is a function of the duration dur of the stimulation pulse and the time constant $RC_{output}$. This means that if the duration dur of the stimulation pulse and the time constant $RC_{output}$ are constant for different stimulation pulse amplitudes the polarization Pol depends only on the stimulation pulse amplitude $U_{stim}$ and this dependency is linear.

Studies on animals show that the evoked response signal amplitude ER is fairly constant for different stimulation pulse amplitudes $U_{stim}$ and independent of the stimulation pulse duration dur. This is illustrated in FIG. 2, which shows the electrode signal (IEGM) for different stimulation amplitudes as a function of time. Thus the electrode signals are recorded from immediately after the stimulation complex is delivered, time 0, and until approximately 70 msec after the stimulation. Curve A is obtained for a stimulation pulse amplitude of 0.6 V, curve B is obtained for a stimulation pulse amplitude of 1.5 V, curve C is obtained for a stimulation pulse amplitude of 3.0 V, and curve D for a stimulation pulse amplitude of 4.5 V.

Each curve represents the sum of the evoked response signal and the polarization signal. As the evoked response signal is essentially constant it is apparent from the figure that the polarization signal varies significantly with the used stimulation pulse amplitude.

At the top of FIG. 2 the evoked response signals with the polarization subtracted are shown.

FIG. 3 shows a block diagram of the principal layout of the detector according to the invention incorporated in a heart stimulator. The stimulator includes a pulse generator 2 which through a lead 6 is connected to the heart 8 of a patient. The pulse generator 2 is controlled by a control unit 19 to produce stimulation pulses of varying amplitudes which through the lead 6 are transferred to the heart 8. The evoked response detector 4 is also connected to the lead 6. The evoked response detector 4 includes a filter, a measuring and memory unit 10 and the filtered electrode signal is supplied to a calculating 16 and to an analyzing unit 12 for determining the polarization and the true evoked response signal.

The measuring and memory unit 10 is disconnected by the switch 11 from the lead 6 during stimulation. As a consequence the electrode signal obtained before the stimulation in question will be stored in the measurement and memory unit 10. When the evoked response detector is enabled after a stimulation the difference between the electrode signal before stimulation and after is supplied to the calculation unit 12 analyzing means 12, 16.

A timer 14, 13 provided for determining an evoked response window during which the electrode signal is measured and stored. This evoked response window normally extends from 15 to 55 msec after stimulation.

As an alternative an averaging unit 18 can be provided for forming the average value of a predetermined number of measured electrode signals.

FIG. 4 shows in more detail one embodiment of the evoked response detector according to the invention. The heart electrode signal picked up by the lead 6 in FIG. 3 is then supplied to a highpass filter 20. An amplifier 22 and an A/D converter 24 are provided for amplifying and A/D converting respectively the filtered signal. A digital signal processor 26 calculates the polarization as will be described more in detail below and determines the true evoked response signal.

Thus in the embodiment shown in FIG. 4 the algorithm for determining whether an evoked response is detected or not is implemented in software by use of a microprocessor.

Instead of a microprocessor this algorithm can also be implemented in random logic, which means realization by ordinary logic element, that is logic gates.

The detector according to the invention can also be implemented in the heart stimulator electronics by use of switched capacitor (SC) technique. The algorithm is then implemented in SC technique, where different capacitors serve as memory elements for storing the different electrode potentials and SC-adding, subtracting and multiplying circuits are used for performing the necessary calculations as explained above.

In the detector according to the invention the polarization is calculated for determining the true evoked response signal for determining whether capture is obtained or not, and possibly for activating an AUTOCAPTURE™ function of the heart stimulator in question. A requirement is then that the stimulation threshold value is previously known, and this threshold value can be determined by the technique according to the co-pending WO 99/65566.To be able to decide whether the AUTOCAPTURE™ function can be activated or not the polarizationr signal for the lowest stimulation amplitude, e.g. 0.3 V, is determined. In this example it is assumed that the amplitude resolution is 0.3 V. The mean value of the amplitude of the evoked response signal (with the polarization signal subtracted), is calculated for a low stimulation amplitude, e.g. 0.6 V, and a high stimulation amplitude, e.g. 4.5 V. The duration of the stimulation pulses is supposed to be equal to the pulse duration when determining the stimulation threshold value.

If the stimulation threshold value is less than a predetermined value X, e.g. ≡2 V, the detector illustrated in FIGS. 3 and 4, operates as follows.

The unipolar IEGM measured between the electrode tip of the implanted ventricular lead 6 and the pacemaker casing is filtered by an analog bandpass filter with a cut-off frequency of 1 Hz to 130 Hz. Before the emission of a stimulation pulse, with a unipolar or bipolar electrode configuration, the IEGM signal is sampled. The mean value of these samples is calculated and represents the DC level. The stimulation pulse followed by the fast discharge pulse is then delivered.

The evoked response detector is blanked a predetermined time from the beginning of the stimulation pulse, for example during 15 msec. When the blanking time is terminated the picked up IEGM signal is sampled and digitized. The sampling frequency can be e.g. 512 Hz and the sampling occurs for a predetermined time interval called the evoked response window. The DC level is subtracted from each sample.

To remove the polarization, a certain amount of polarization, achieved from a polarization algorithm described below, is subtracted from the measured electrode signal (IEGM). The number of polarization steps Polstep equals the stimulation amplitude divided by the voltage step which the heart stimulator in question uses between consecutive stimulation amplitudes. For example, if the stimulation amplitude is 4.5 V and the voltage step is 0.3 V, 15 $Pol_{step}$ signals will be subtracted. Thereafter the mean value of all samples, after subtractions, is calculated, and this mean value represents the mean amplitude of the evoked response signal.

As mentioned above the detector according to the invention is based on the fact that the true evoked response signal is independent of the stimulation amplitude, and this true evoked response signal ER equals the signal sampled during the evoked response window with the polarization signal subtracted. Thus, the difference in the measured electrode signal in the evoked response window is mainly due to the polarization. The detector subtracts the polarization signal resulting for the stimulation amplitude in question before it decides whether capture has occurred or not. The polarization signal is determined with the algorithm below.

The so called Vario cycle is started as usual, i.e.
1. Stimulation starts at the highest amplitude, e.g. 4.5 V, and is continued in voltage steps down to the lowest amplitude, which is equal to the stimulation threshold amplitude at the pulse width chosen plus one voltage step.
2. A predetermined number of samples are taken before the highest and lowest stimulation pulse in the Vario cycle and the average value is calculated to get the DC level.
3. The measured electrode signal (IEGM) is sampled during the evoked response window following the highest and lowest stimulation pulses.
4. The DC level is subtracted from both the measured electrode signals to get the real amplitudes of these signals.
5. The achieved signals for the lowest stimulation amplitude is then subtracted from the achieved signal from the highest stimulation amplitude.
6. The resulting signal will be divided by the number of voltage steps between the highest stimulation amplitude and the lowest stimulation amplitude to get the $Pol_{step}$ signal. For instance, if the highest amplitude is 4.5 V, the lowest stimulation amplitude is 0.9 and the step is 0.3 V, the resulting signal will be divided by $$\frac{4.5 - 0.9}{0.3} = 12.$$

The steps 1–6 above are repeated a predetermined number of times and the average value of Polstep is calculated. This value is then stored and used to eliminate the polarization from the measured electrode signal for each subsequent heart beat when the detector is working.

If the stimulation threshold value>X the polarization step $Pol_{step}$ is determined by stimulating a predetermined number of times with pulses of an amplitude equal to the threshold value minus 0.3 V. In this case capture is, of course, not obtained and the mean value of the measured electrode signals is stored as $Pol_{thres-0.3}$.

The polarization for a stimulation pulse of 0.3 V is then calculated as $$Pol_{0.3} = \frac{Pol_{thresh-0.3}}{K}$$

where $K = \frac{U_{stimthresh-0.3}}{0.3}$

The quantity $Pol_{step}$ can be calculated in different ways, and the above described methods are just examples of such calculations, but it is important that the stimulation amplitude is changed in comparatively small steps in order to get correct DC levels.

When using just a high stimulation amplitude and a low stimulation amplitude for determining the $Pol_{step}$ there should be a big step between these two amplitudes but by stimulating several times at both the high and the low amplitude before the sampling takes place, there will be no big step before the signals used in the calculations of the $Pol_{step}$. Incorrect DC levels will, of course, give false $Pol_{step}$ signals.

When the $Pol_{step}$ signal is calculated an evoked response sensitivity test can be performed to determine e.g. if an AUTOCAPTURE™ function can be activated. This test is performed on the true evoked response signal, that is the measured signal with the polarization signal subtracted. If the absolute amplitude of the true evoked response signal is larger than a predetermined value an evoked response threshold level can be set and the AUTOCAPTURE™ function be activated.

An example of how such an evoked response sensitivity test can be performed is as follows:

1. A predetermined number of stimulation pulses of high amplitude, preferably the highest available amplitude, e.g. 4.5 V is emitted, and the measured electrode signals are sampled in the evoked response window. The DC level and the corresponding number of $Pol_{step}$ signals are subtracted. Thus, if the stimulation amplitude is 4.5 V and the voltage step is 0.3 V the number of $Pol_{step}$ will be 15. Then stimulation is performed with low amplitude, preferably the lowest stimulation amplitude, and the DC level and corresponding number of $Pol_{step}$ are subtracted. The number of $Pol_{step}$ will be equal to the low stimulation amplitude divided by the voltage step.
2. The average amplitude of the resulting signal $ER_{highamp}$ for the high stimulation amplitude pulses is calculated.
3. The average amplitude of the resulting signal $ER_{lowamp}$ for the low stimulation amplitude pulses is calculated.
4. If max ($ER_{highamp}$, $ER_{lowamp}$)<a predetermined value AUTOCAPTURE™ can be activated and evoked response threshold value be set according to predetermined rules.

Evoked response signal amplitudes below this threshold value will then be considered as capture, and evoked response signal amplitudes above this threshold level as loss of capture, i.e. a backup pulse of higher amplitude will be emitted. It should be noted that the signals in question are negative.

If the stimulation threshold value>X, $ER_{lowamp}$, e.g. $ER_{0.6}$, must be calculated as follows if the threshold value exceeds 0.3 V:

$$ER_{0.6} = ER_{4.5} - 13 \times Pol_{0.3}(=Pol_{step}).$$

If the stimulation threshold value equals 0.3 V, $$ER_{0.6} = ER_{thresh+0.3}.\text{ In this case } ER_{0.6} = ER_{lowamp}.$$

Although modifications and changes may be suggested by those skilled in the art, it is the intention of the inventors to embody within the patent warranted hereon all changes and modifications as reasonably and properly come within the scope of their contribution to the art.

We claim:

1. A heart stimulator comprising:
   a pulse generator which emits stimulation pulses, each having an amplitude;
   an electrode lead connected to said pulse generator and adapted for introduction into a patient to deliver said stimulation pulses to the patient's heart, and for picking up respective signals representing polarization of the heart immediately after each of said stimulation pulses;
   a control unit connected to said pulse generator for controlling said pulse generator to emit said stimulation pulses with respectively different amplitudes, including a high amplitude stimulation pulse preceding a low amplitude stimulation pulse, said low amplitude stimulation pulse having an amplitude equal to a known stimulation threshold voltage plus a predetermined voltage step, and said high amplitude stimulation pulse having an amplitude above the amplitude of said low amplitude stimulation pulse;
   an evoked response detector including a measurement and memory unit connected to said electrode lead, a calculating unit connected to an output of said measurement and memory unit, and an analyzing unit connected to an output of said calculating unit;
   said measurement and memory unit measuring and storing respective signals picked up by said electrode lead immediately after said high amplitude stimulation pulse and said low amplitude stimulation pulse, as well as measuring and storing respective signals picked up said electrode lead immediately following respective subsequent stimulation pulses emitted after said low amplitude stimulation pulse;
   said calculating unit determining a first difference between the respective signals picked up by said electrode lead immediately after said high amplitude stimulation pulse and said low amplitude stimulation pulse, a second difference between the amplitude of said high amplitude stimulation pulse and the amplitude of said low amplitude stimulation pulse, and a quotient of said first difference and said second difference; and
   said analyzing unit determining whether an evoked response has occurred to respective ones of said subsequent stimulation pulses by, for each subsequent stimulation pulse, determining a polarization signal by multiplying the amplitude of the subsequent stimulation pulse by said quotient, and subtracting said polarization signal from the signal picked up by the electrode lead immediately following the subsequent stimulation pulse.

2. A heart stimulator as claimed in claim 1 wherein said control unit controls said pulse generator to emit said high amplitude stimulation pulse preceding said low amplitude stimulation pulse a plurality of times, and wherein said measuring and memory unit measures the respective signals picked up by said electrode lead for each of said times, and wherein said calculating unit calculates said quotient for each of said times to obtain a plurality of quotients, and forms an average quotient value of said plurality of quotients, and wherein said analyzing unit uses said average quotient value as said quotient for determining whether an evoked response has occurred to said subsequent stimulation pulses.

3. A heart stimulator as claimed in claim 1 wherein said measuring and memory unit samples the respective signals picked up by said electrode lead after each of said high amplitude stimulation pulse, said low amplitude stimulation pulse, and said subsequent stimulation pulses, with a predetermined sampling frequency during a predetermined time interval after emission of the stimulation pulse, and calculates an average value of said sample values for use by said calculating unit for determining said first difference.

4. A heart stimulator as claimed in claim 1 wherein said measuring and memory unit measures an electrode signal picked up by said electrode lead before emission of each of said subsequent stimulation pulses to determine a d.c. level which is subtracted from the respective signals picked up after emission of each subsequent stimulation pulse.

5. A heart stimulator as claimed in claim 4 wherein said measuring and memory unit measures respective electrode signals picked up by said electrode lead before emission of each of said high amplitude stimulation pulse and said low amplitude stimulation pulse, and wherein said calculating unit determines an average value of said electrode signals picked up before emission of said high amplitude stimulation pulse and said low amplitude stimulation pulse as a d.c. level, and subtracts said d.c. level from the respective signals picked up after emission of said high amplitude stimulation pulse and said low amplitude stimulation pulse.

6. A heart stimulator as claimed in claim 1 wherein said analyzing unit emits an evoked response signal representing subtraction of said polarization signal from said signal picked up by said electrode lead following the subsequent stimulation pulse, and further comprising a comparator which compares said evoked response signal to a predetermined value to determine whether capture has occurred.

7. A heart stimulator as claimed in claim 6 wherein said control unit controls said pulse generator to emit said high amplitude stimulation pulse preceding said low amplitude stimulation pulse a plurality of times, and wherein said analyzing unit produces said evoked response signal for each of said times, thereby producing a plurality of evoked response signals, and forms an average value of said plurality of evoked response signals, and wherein said comparator is supplied with said average value for comparison with said predetermined value.

8. A heart stimulator comprising:

a pulse generator which emits stimulation pulses, each having an amplitude;

an electrode lead connected to said pulse generator and adapted for introduction into a patient to deliver said stimulation pulses to the patient's heart, and for picking up respective signals representing polarization of the heart immediately after each of said stimulation pulses;

a control unit connected to said pulse generator for controlling said pulse generator to emit said stimulation pulses with respectively different amplitudes including a high amplitude stimulation pulse preceding a succession of lower amplitude stimulation pulses, said succession of lower amplitude stimulation pulses having respective amplitudes successively lowered from the amplitude of said high amplitude stimulation pulse by a predetermined voltage step so that the respective lower amplitude stimulation pulses have amplitudes equal to a known stimulation threshold voltage plus one or more of said voltage steps;

an evoked response detector including a measuring and memory unit connected to said electrode lead, a calculating unit connected to an output of said measuring and memory unit, and an analyzing unit connected to an output of said calculating unit;

said measurement and memory unit measuring and storing respective signals picked up by said electrode lead immediately after said high amplitude stimulation pulse and each of said lower amplitude stimulation pulses;

said calculating unit, for each of said lower amplitude stimulation pulses, determining a difference between the signal picked up by said electrode lead after said high amplitude stimulation pulse and the signal picked up by said electrode lead after the respective lower amplitude stimulation pulse and for dividing said difference by the number of voltage steps used to produce the lower amplitude stimulation pulse, and determining and storing a magnitude of polarization per voltage step; and said analyzing unit determining whether an evoked response has occurred to subsequent stimulation pulses, after a last of said lower amplitude stimulation pulses, by determining a polarization signal by forming a quotient between the amplitude of the subsequent stimulation pulse and said voltage step and multiplying said quotient by said polarization per voltage step, and subtracting said polarization signal from the signal picked up by said electrode lead immediately following said subsequent stimulation pulse.

9. A heart stimulator as claimed in claim 8 wherein said control unit controls said pulse generator to emit a plurality of series of stimulation pulses, each of said series starting with said high amplitude stimulation pulse and ending with a last of said lower amplitude stimulation pulses, and wherein said calculating unit determines said polarization per voltage step from respective signals picked up by said electrode lead for each series, to obtain a plurality of values for the polarization pervoltage step, and forms an average value of said plurality of values, and wherein said analyzing unit uses said average value as said polarization per voltage step for determining whether said evoked response has occurred.

10. A heart stimulator as claimed in claim 8 wherein said measuring and memory unit samples the respective signals picked up by said electrode lead after each of said high amplitude stimulation pulse, said low amplitude stimulation pulse, and said subsequent stimulation pulses, with a predetermined sampling frequency during a predetermined time interval after emission of the stimulation pulse, and calculates an average value of said sample values for use by said calculating unit for determining said first difference.

11. A heart stimulator as claimed in claim 8 wherein said measuring and memory unit measures an electrode signal picked up by said electrode lead before emission of each of said subsequent stimulation pulses to determine a d.c. level which is subtracted from the respective signals picked up after emission of each subsequent stimulation pulse.

12. A heart stimulator as claimed in claim 11 wherein said measuring and memory unit measures respective electrode signals picked up by said electrode lead before emission of each of said high amplitude stimulation pulse and said lower amplitude stimulation pulses, and wherein said calculating unit determines an average value of said electrode signals picked up before emission of said high amplitude stimulation pulse and said lower amplitude stimulation pulses as a d.c. level, and subtracts said d.c. level from the respective signals picked up after emission of said high amplitude stimulation pulse and said lower amplitude stimulation pulses.

13. A heart stimulator as claimed in claim 8 wherein said analyzing unit emits an evoked response signal representing subtraction of said polarization signal from said signal picked up by said electrode lead following the subsequent stimulation pulse, and further comprising a comparator which compares said evoked response signal to a predetermined value to determine whether capture has occurred.

14. A heart stimulator as claimed in claim 13 wherein said control unit controls said pulse generator to emit said high amplitude stimulation pulse preceding said lower amplitude stimulation pulses a plurality of times, and wherein said analyzing unit produces said evoked response signal for each of said times, thereby producing a plurality of evoked response signals, and forms an average value of said plurality of evoked response signals, and wherein said comparator is supplied with said average value for comparison with said predetermined value.

15. A heart stimulator comprising:

a pulse generator which emits stimulation pulses, each having an amplitude;

an electrode lead connected to said pulse generator and adapted for introduction into a patient to deliver said stimulation pulses to the patient's heart, and for picking up respective signals representing polarization of the heart immediately after each of said stimulation pulses;

a control unit connected to said pulse generator for controlling said pulse generator to emit said stimulation pulses with respectively different amplitudes, including a delivered stimulation pulse having an amplitude below a stimulation threshold voltage by a voltage step;

an evoked response detector including a measuring and memory unit connected to said electrode lead, a calculating unit connected to an output of said measuring and memory unit, and an analyzing unit connected to an output of said calculating unit;

said measurement and memory unit measuring and storing a signal picked up by said electrode lead immediately following said delivered stimulation pulse;

said calculating unit determining a quantity $Pol_{step} = U_{measlow}/m$, wherein $U_{measlow}$ is a voltage of said signal and m is a quotient between the amplitude of said delivered stimulation pulse and said voltage step; and said analyzing unit determining whether an evoked response has occurred to subsequent stimulation pulses emitted after said delivered stimulation pulse by, for each subsequent stimulation pulse, determining a polarization signal by determining a quotient between the amplitude of the subsequent stimulation pulse and said voltage step and multiplying said quotient by $Pol_{step}$, and subtracting said polarization signal from the signal picked up by said electrode lead immediately following said subsequent stimulation pulse.

16. A heart stimulator as claimed in claim 15 wherein said measuring and memory unit samples the respective signals picked up by said electrode lead after each of said high amplitude stimulation pulse, said low amplitude stimulation pulse, and said subsequent stimulation pulses, with a predetermined sampling frequency during a predetermined time interval after emission of the stimulation pulse, and calculates an average value of said sample values for use by said calculating unit for determining said first difference.

17. A heart stimulator as claimed in claim 15 wherein said measuring and memory unit measures an electrode signal picked up by said electrode lead before emission of each of said subsequent stimulation pulses to determine a d.c. level which is subtracted from the respective signals picked up after emission of each subsequent stimulation pulse.

18. A heart stimulator as claimed in claim 17 wherein said measuring and memory unit measures respective electrode signals picked up by said electrode lead before emission of said delivered stimulation pulse, and wherein said calculating unit determines an average value of said electrode signals picked up before emission of said delivered stimulation pulse as a d.c. level, and subtracts said d.c. level from the respective signals picked up after emission of said delivered stimulation pulse.

19. A heart stimulator as claimed in claim 15 wherein said analyzing unit emits an evoked response signal representing subtraction of said polarization signal from said signal picked up by said electrode lead following the subsequent stimulation pulse, and further comprising a comparator which compares said evoked response signal to a predetermined value to determine whether capture has occurred.

20. A heart stimulator as claimed in claim 19 wherein said control unit controls said pulse generator to emit said delivered stimulation pulse a plurality of times, and wherein said analyzing unit produces said evoked response signal for each of said times, thereby producing a plurality of evoked response signals, and forms an average value of said plurality of evoked response signals, and wherein said comparator is supplied with said average value for comparison with said predetermined value.

* * * * *